United States Patent
Yan et al.

(10) Patent No.: US 9,597,302 B1
(45) Date of Patent: Mar. 21, 2017

(54) COMBINATION OF DOFETILIDE AND MEXILETINE FOR THE PREVENTION AND TREATMENT OF ATRIAL FIBRILLATION

(71) Applicant: Heart Rhythm Solutions, Inc., Newtown Square, PA (US)

(72) Inventors: Ganxin Yan, Rosemont, PA (US); Jian-Zeng Dong, Beijing (CN); Chang-Sheng Ma, Beijing (CN)

(73) Assignee: Heart Rhythm Solutions, Inc., Newtown Square, PA (US)

( * ) Notice: Subject to any disclaimer, the term of this patent is extended or adjusted under 35 U.S.C. 154(b) by 0 days.

(21) Appl. No.: 14/922,529

(22) Filed: Oct. 26, 2015

Related U.S. Application Data

(60) Provisional application No. 62/222,973, filed on Sep. 24, 2015.

(51) Int. Cl.
| | | |
|---|---|---|
| *A61K 31/18* | (2006.01) | |
| *A61K 31/138* | (2006.01) | |
| *A61K 9/00* | (2006.01) | |
| *A61K 9/48* | (2006.01) | |

(52) U.S. Cl.
CPC ............ *A61K 31/18* (2013.01); *A61K 9/0053* (2013.01); *A61K 9/48* (2013.01); *A61K 31/138* (2013.01)

(58) Field of Classification Search
USPC ........................................................ 514/605
See application file for complete search history.

(56) References Cited

PUBLICATIONS

Todt et al. publication Eur. J. Pharmacol., 1994, 14:265(1-2): 43-52.*
Guo et al, "Prevalence, incidence, and lifetime risk of atrial fibrillation in China: new insights into the global burden of atrial fibrillation," Chest, vol. 147, pp. 109-119 (2015).
Chei et al., "Prevalence and Risk Factors of Atrial Fibrillation in Chinese Elderly: Results from the Chinese Longitudinal Healthy Longevity Survey," Chin Med J (Engl), vol. 128, pp. 2426-2432 (2015).
Chugh et al., "Worldwide epidemiology of atrial fibrillation: a Global Burden of Disease 2010 Study," Circulation, vol. 129, pp. 837-847 (2014).
Colilla et al., "Estimates of current and future incidence and prevalence of atrial fibrillation in the U.S. adult population,"Am J Cardiol, vol. 112, pp. 1142-1147 (2013).
Suttorp et al., "Efficacy and safety of a new selective class III antiarrhythmic agent dofetilide in paroxysmal atrial fibrillation or atrial flutter," Am J Cardiol, vol. 69, pp. 417-419 (1992).
Rasmussen et al., "Dofetilide, a novel class III antiarrhythmic agent," J Cardiovasc Pharmacol, vol. 20, Suppl 2, pp. S96-S105 (1992).
Zimetbaum, "Antiarrhythmic drug therapy for atrial fibrillation," Circulation, vol. 125, pp. 381-389 (2012).
Qin et al., "Comparative effectiveness of antiarrhythmic drugs for rhythm control of atrial fibrillation," J Cardiol, (2015).
Aktas et al., "Dofetilide-induced long QT and torsades de pointes," Ann Noninvasive Electrocardiol, vol. 12, pp. 197-202 (2007).
Qi et al., "Heterogeneous distribution of INa-L determines interregional differences in rate adaptation of repolarization," Heart Rhythm, vol. 12, pp. 1295-1303 (2015).
Badri et al., "Mexiletine Prevents Recurrent Torsades de Pointes in Acquired Long QT Syndrome Refractory to Conventional Measures," JACC: Clinical Electrophysiology, vol. 1, pp. 315-322 (2015).
Yan et al., "Phase 2 early afterdepolarization as a trigger of polymorphic ventricular tachycardia in acquired long-QT syndrome: direct evidence from intracellular recordings in the intact left ventricular wall," Circulation, vol. 103, pp. 2851-2856 (2001).
Talbot et al., "Treatment of ventricular arrhythmias with mexiletine (Ko 1173)," Lancet, vol. 2, pp. 399-404 (1973).
Campbell et al., "Mexiletine (Ko 1173) in the management of ventricular dysrhythmias," Lancet, vol. 2, pp. 404-407 (1973).
Miller et al., "Braunwald's Heart Disease: A Textbook of Cardiovascular Medicine," Therapy for Cardiac Arrhythmias, Elsevier Publisher, pp. 693 (2014).
January et al., "2014 AHA/ACC/HRS guideline for the management of patients with atrial fibrillation: executive summary: a report of the American College of Cardiology/American Heart Association Task Force on practice guidelines and the Heart Rhythm Society," Circulation, vol. 130, pp. 2071-2104 (2014).
Yan et al., "Cellular basis for the electrocardiographic J wave," Circulation, vol. 93, pp. 372-379 (1996).
Wang et al., "Preclinical assessment of drug-induced proarrhythmias: role of the arterially perfused rabbit left ventricular wedge preparation," Pharmacol Ther, vol. 119, pp. 141-151 (2008).
Ono et al., "Comparison of the inhibitory effects of mexiletine and lidocaine on the calcium current of single ventricular cells," Life Sci, vol. 39, pp. 1465-1470 (1986).
Gottlieb et al., "Cardiodepressant effects of mexiletine in patients with severe left ventricular dysfunction," Eur Heart J, vol. 13, pp. 22-27 (1992).
Shaw, "NDA 20-931, Tykosyn (dofetilide) for Supraventricular Arrhythmias (SVA), Approvability," Department of Health & Human Services Memo, Jan. 19, 1999, downloaded from web page: http://www.accessdata.fda.gov/drugsatfda_docs/nda/99/20-931_Tikosyn_admindocs_P2.pdf, Download date: Jan. 2016, original posting date: unknown, 36 pages.
"TikosynÒ (dofetilide), NDA 20-931, Risk Evaluation and Mitigation Strategy Development," Pfizer Labs, Division of Pfizer Inc., New York, NY (2013).

* cited by examiner

*Primary Examiner* — Rei-Tsang Shiao
(74) *Attorney, Agent, or Firm* — Panitch Schwarze Belisario & Nadel LLP

(57) ABSTRACT

Effective and safe pharmaceutical composition and method for treating atrial fibrillation are described. The combined use of dofetilide and mexiletine resulted in an enhanced efficacy in the prevention and treatment of atrial fibrillation with markedly reduced risk of the life-threatening ventricular arrhythmia TdP.

19 Claims, 6 Drawing Sheets

COMBINATION OF DOFETILIDE AND MEXILETINE FOR THE PREVENTION AND TREATMENT OF ATRIAL FIBRILLATION

CROSS REFERENCE TO RELATED APPLICATIONS

This application is entitled to priority pursuant to 35 U.S.C. §119(e) to U.S. Provisional Patent Application No. 62/222,973, filed Sep. 24, 2015, the disclosure of which is hereby incorporated by reference herein in its entirety.

BACKGROUND OF THE INVENTION

Atrial fibrillation is the most common abnormal heart rhythm affecting approximately 5.2 million people in United States, more than 10 million in China[1,2] and 33 million world-wide.[3] Despite improvements in primary and secondary prevention of coronary artery disease, and effective treatment of hypertension and other heart diseases, the prevalence of atrial fibrillation continues to rise. The rise in atrial fibrillation may, at least in part, be due to the longer average life span of humans. It is projected that atrial fibrillation prevalence will increase to 12.1 million cases in 2030 in the US.[4] Atrial fibrillation predisposes patients, particularly elders, to a higher risk for stroke, heart failure, and death. About 35% of all strokes in the U.S. annually are attributed to atrial fibrillation.

One of the important treatment approaches for atrial fibrillation is to restore and maintain normal heart rhythm. Currently, there are two major clinical approaches for this treatment: (1) drug therapy; and (2) radiofrequency ablation. Both approaches have advantages and disadvantages, and both are insufficient to eliminate atrial fibrillation.

There is a higher reoccurrence rate of atrial fibrillation when patients are treated with drug therapy than radiofrequency ablation due to relatively poor efficacy and incidence of adverse effects of drugs for the management of atrial fibrillation. Although dofetilide has been used for the treatment of atrial fibrillation for more than 20 years,[5,6] its annual prescription represents only 2% of antiarrhythmic drug prescription (versus another antiarrhythmic drug amiodarone that represents 45%) among only a few antiarrhythmic drugs available in the market.[7] In addition, dofetilide has not been approved for use in Europe and China. The major reasons for insignificant use of dofetilide by clinicians include: its relatively suboptimal efficacy;[8] a risk of QT prolongation leading to life-threatening ventricular arrhythmias termed torsade de points (TdP),[9] as a result, a 3-day mandatory in-hospital loading period required by the US FDA; and the doctor who prescribes dofetilide and the hospital must have gone through special dofetilide training.

First line treatment approaches to TdP include removal of the offending causes and avoidance of QT-prolonging agents, such as treatment with dofetilide. It has been recently suggested that inhibition of the late sodium current ($I_{Na-L}$) may be an effective treatment approach to terminate TdP in acquired long QT syndromes (LQTS) specifically by dofetilide.[10,11]

There remains a need for novel effective and safe methods and pharmaceutical compositions for treating or preventing atrial fibrillation and related symptoms. Specifically, there is a need for novel methods and pharmaceutical compositions that provide more effective prevention and/or treatment of atrial fibrillation in patients in need thereof, while reducing the risk of adverse effects, such as incidence of TdP. Such methods and pharmaceutical compositions are described in the present application.

BRIEF SUMMARY OF THE INVENTION

It is now discovered that mexiletine not only is an effective suppressor of TdP via inhibition of the late sodium current, but also acts synergistically with dofetilide, an antiarrhythmic drug for the treatment of atrial fibrillation, to result in a major improvement in the treatment of atrial fibrillation, with a decreased risk of ventricular arrhythmias. Combined use of dofetilide and mexiletine can expand the dose range of dofetilide bidirectionally (i.e. a smaller minimal effective dose to a higher safe dose) in the treatment of atrial fibrillation because of the synergistic effect of both drugs in suppression of atrial fibrillation and reduction of risks of ventricular proarrhythmias. This will greatly enhance capability of clinicians to treat atrial fibrillation in a conservative way rather than via invasive procedures like radiofrequency ablation because both efficacy and safety profiles of the combined use of dofetilide and mexiletine are markedly improved.

In one general aspect, embodiments of the invention relate to a pharmaceutical composition for treating and/or preventing atrial fibrillation or a symptom associated therewith in a subject in need thereof, which comprises an effective amount of dofetilide, an effective amount of mexiletine, and a pharmaceutically acceptable carrier.

In another general aspect, embodiments of the invention relate to a method of treating and/or preventing atrial fibrillation or a symptom associated therewith in a subject in need thereof, comprising administering to the subject an effective amount of dofetilide and an effective amount of mexiletine. The effective amount of mexiletine can be administered together with the effective amount of dofetilide in the same pharmaceutical composition such as that according to an embodiment of the invention. The effective amount of mexiletine can also be administered separately from the effective amount of dofetilide in a different pharmaceutical composition, so long as the dosing schedules of dofetilide and mexiletine overlap, such that the administered mexiletine is effective to reduce the risk of adverse effects associated with the administered dofetilide and/or to enhance the efficacy of the administered dofetilide.

In a preferred embodiment of the invention, a method of the invention results in more efficacious treatment of atrial fibrillation or a symptom associated therewith with reduced adverse effects in a subject in need thereof than the conventional treatment with dofetilide alone. For example, according to an embodiment of the invention, a method of the invention significantly increases atrial effective refractory period (ERP) in comparison to that achieved by the administration of the effective amount of dofetilide alone, and reduces at least one of early afterdepolarization (EAD), EAD-dependent R-on-T extrasystoles, and Torsades de Pointes (TdP) induced by the administration of the effective amount of dofetilide, in a subject in need thereof.

A further aspect of the invention relates to a method of manufacturing a pharmaceutical composition, comprising combining an effective amount of dofetilide, an effective amount of mexiletine, and a pharmaceutically acceptable carrier to obtain the pharmaceutical composition.

Other aspects, features and advantages of the invention will be apparent from the following disclosure, including the detailed description of the invention and its preferred embodiments and the appended claims.

BRIEF DESCRIPTION OF THE SEVERAL
VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 illustrates the effects of different combinations of dofetilide (D) with mexiletine (M) on atrial action potential duration at 90% of repolarization (APD90) in rabbits at basic cycle lengths (BCL) of 1000 ms (FIG. 1A) or 500 ms (FIG. 1B), wherein, NS indicates no statistical significance, SEM for error bars, n=9 for dofetilide at 3 nM and dofetilide at 3 nM plus mexiletine at 10 µM, n=5 for dofetilide at 10 nM and dofetilide 10 nM plus mexiletine at 30 µM;

FIG. 2 illustrates the effect of dofetilide (D) and dofetilide plus mexiletine (M) on atrial effective refractory period (ERP) in rabbits at 3 nM of D with or with 10 µM of M (FIG. 2A) or 10 nM of D with or with 30 µM of M (FIG. 2B), wherein, * indicates p<0.05 and ** indicates p<0.01 as compared with the ERP in the dofetilide group, # indicates that 1 out of 9 atrial wedge preparations paced at 2 Hz lost excitation, & indicates that 4 out of 7 atrial wedge preparations paced at 3.3 Hz lost excitation, note also that the y-axis scales are different in FIG. 2A and FIG. 2B;

Figure 5:
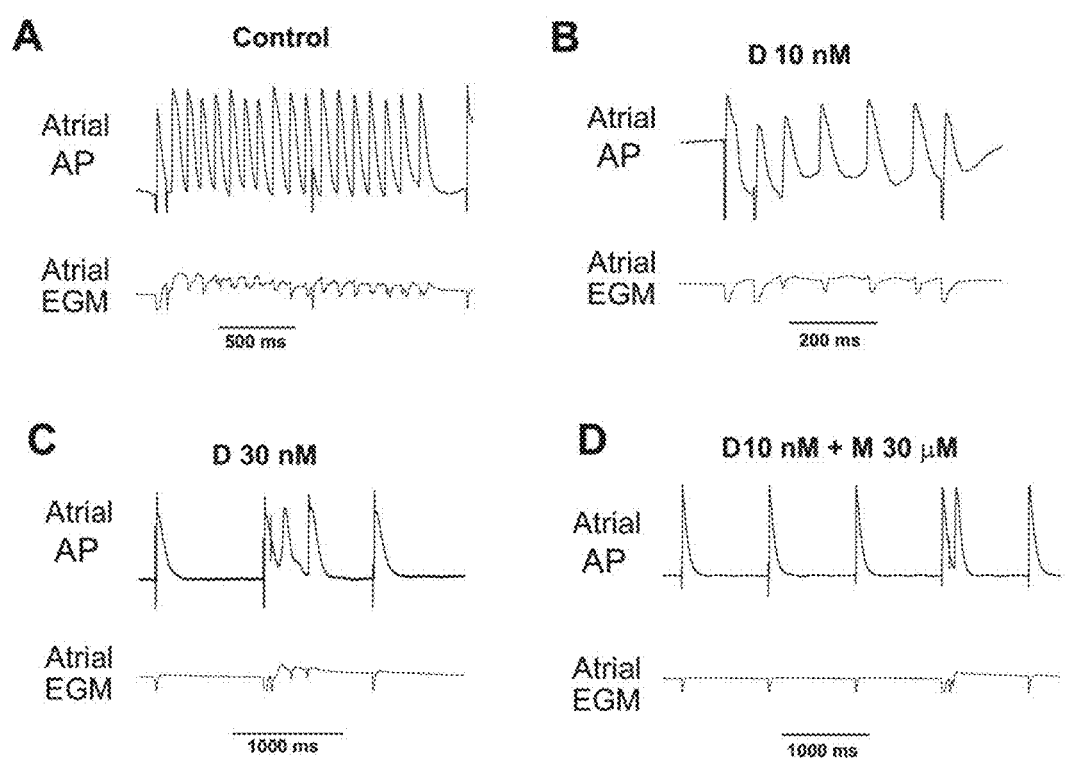
Figure 6:
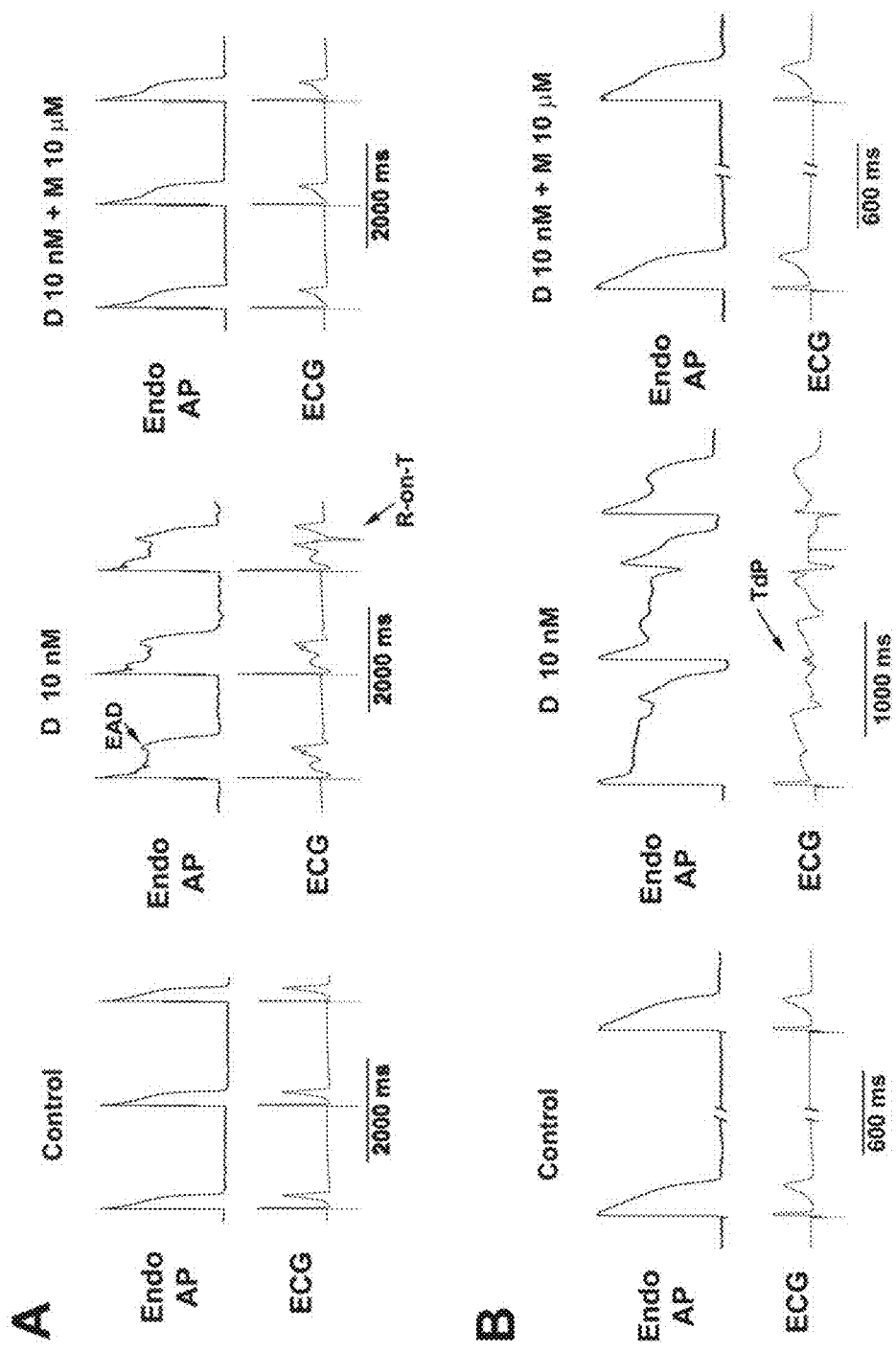

FIG. 5 illustrates, by way of atrial pacing and electrogram readings, an example of the effect of dofetilide (D) and dofetilide plus mexiletine (M) on atrial fibrillation: in one atrial wedge preparation, atrial fibrillation was readily induced by single extrastimuli (FIG. 5A), dofetilide alone at relatively higher concentrations, e.g., 10 nM (FIG. 5B) and 30 nM (FIG. 5C), failed to suppress induction of atrial fibrillation and premature beats, while dofetilide (10 nM) plus mexiletine (30 µM) completely abolished atrial fibrillation (FIG. 5D), wherein AP refers to action potential, and EGM refers to electrogram; and FIG. 6 illustrates, by way of atrial pacing and electrogram readings, examples of the effect of mexiletine (M) on dofetilide (D)-induced early afterdepolarization (EAD), EAD-dependent R-on-T extrasystoles, and Torsades de Pointes (TdP) in arterially-perfused rabbit left ventricular wedges: FIG. 6A shows that mexiletine at 10 µM abolished dofetilide-induced EAD and R-on-T extrasystoles; FIG. 6B shows that mexiletine at 10 µM abolished dofetilide-induced EAD and TdP.

DETAILED DESCRIPTION OF THE
INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, the name of a compound, such as dofetilide and mexiletine, can encompass all possibly existing isomeric forms (e.g., optical isomer, enantiomer, diastereomer, racemate or racemic mixture), esters, prodrugs, metabolite forms, pharmaceutically acceptable salts, pharmaceutically acceptable esters, pharmaceutically acceptable amides, and protected derivatives, of the compound.

As used herein, the term "subject" means any animal, preferably a mammal, most preferably a human, to whom will be or has been administered a compound or a pharmaceutical composition according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of, or has been the object of observation or experiment of, treatment or prevention of atrial fibrillation and symptoms associated therewith, more preferably, such a subject is an elderly human subject.

A "subject" as described herein is preferably in need of treatment or prevention of atrial fibrillation and symptoms associated therewith. Atrial fibrillation is an abnormal heart rhythm characterized by irregular and often rapid beating that commonly causes poor blood flow to the body. During atrial fibrillation, the heart's two upper chambers (the atria) beat chaotically and irregularly out of coordination with the two lower chambers (the ventricles) of the heart. Symptoms of atrial fibrillation include, for example, heart palpitations, dizziness, light-headedness, fainting, shortness of breath, chest pain, anginal chest pain, exercise intolerance, and swelling of the extremities. Although episodes of atrial fibrillation can come and go without causing symptoms, atrial fibrillation may lead to blood clots forming in the heart that may circulate to other organs and lead to blocked blood flow (ischemia). Subjects with a history of stroke, transient ischemic attack (TIA), high blood pressure, diabetes, heart failure, rheumatic fever, or a family history of atrial fibrillation can have a higher risk or predisposition to developing atrial fibrillation, or developing complications associated with already diagnosed atrial fibrillation. Thus, such subjects can be in need of prevention of atrial fibrillation, or at increased need of treatment of atrial fibrillation.

As used herein, "treating atrial fibrillation or a symptom associated therewith" means to elicit an antiarrhythmic effect to reset the rhythm or control the rate. For example, the treatment can provide or restore a normal sinus rhythm to an otherwise abnormal heart rhythm, and by so doing providing relief from one or more possible symptoms or other adverse effects caused by the abnormal heart rhythm.

In one embodiment, "treating" refers to an amelioration, prophylaxis, or reversal of a disease or disorder, or at least one discernible symptom thereof. One example is treating atrial fibrillation or a symptom associated therewith by converting the abnormal heart rhythm to a normal sinus rhythm.

In another embodiment, "treating" refers to an amelioration, prophylaxis, or reversal of at least one measurable physical parameter related to the disease or disorder being treated, not necessarily discernible symptom in or by the mammal. For example, treating an abnormal heart rhythm associated with atrial fibrillation or a symptom associated therewith.

In yet another embodiment, "treating" refers to inhibiting or slowing the progression or remodeling of a disease or disorder, either physically, e.g., stabilization of a discernible symptom, physiologically, e.g., stabilization of a physical parameter, or both.

In yet another embodiment, "treating" refers to delaying the onset of a disease or disorder or reduce of the risk of acquiring a disease or disorder, such as atrial fibrillation or a symptom associated therewith. For example, the specified pharmaceutical compositions are administered as a preventative measure to a subject having a predisposition to atrial fibrillation, even though symptoms of atrial fibrillation are absent or minimal.

As used herein, the term "effective amount" of a compound refers to the amount of the compound that elicits the biological or medicinal response in a tissue system, animal or human that is being sought by a researcher, veterinarian, medical doctor or other clinician, which includes alleviation of the symptoms of the disease or disorder being treated. In a preferred embodiment, the effective amount of a compound is sufficient to treat, improve the treatment of, or prophylactically prevent, atrial fibrillation or a symptom associated therewith, but is insufficient to cause significant adverse effects associated with administration of the compound, for example TdP.

In view of the present disclosure, the effective amount of a therapeutically active ingredient according to embodiments of the invention can be determined using methods known to those of ordinary skill in the art. Furthermore, and as is also understood by those of ordinary skill in the art, specific dose levels for any particular subject will depend upon a variety of factors including the age, body weight, general health, sex, diet, time of administration, route of administration, rate of excretion, any additional therapeutic agents administered in combination therewith and the severity of the disease or condition being treated.

Compositions of the invention include one or more therapeutically active ingredients, prodrugs thereof, pharmaceutically acceptable salts thereof, hydrates thereof, solvates thereof and combinations thereof. Specifically, therapeutically active ingredients of present pharmaceutical compositions include dofetilide and mexiletine.

As used herein, the term "dofetilide" refers to the compound N-[4-(2-{[2-(4-methanesulfonamidophenoxy)ethyl](methyl)amino}ethyl)phenyl] methanesulfonamide, having the structure of formula (I)

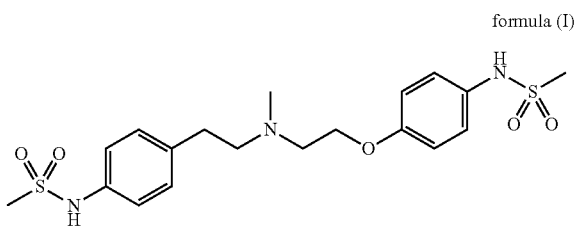

formula (I)

and any prodrug, pharmaceutically acceptable salt, hydrate, solvate, or combination thereof. Dofetilide is distributed by Pfizer, Inc. under the tradename Tikosyn®.

Dofetilide is an antiarrhythmic drug that has been in market for the treatment of atrial fibrillation for more than 20 years.[5,6] However, its efficacy is suboptimal.[8] Administration of dofetilide can also lead to adverse effects, such as an increased risk of QT prolongation, leading to the life-threatening ventricular arrhythmias, TdP triggered by R-on-T extrasystoles via a mechanism of early afterdepolarization (EAD).[12] Although it is uncommon, the risk of TdP by dofetilide can be significantly increased by many factors including hypokalemia, female gender, drug interaction, ventricular hypertrophy and renal function insufficiency.

As used herein, the term "mexiletine" refers to any of the compounds (RS)-1-(2,6-dimethylphenoxy)propan-2-amine or 2-(2-aminopropoxy)-1,3-dimethylbenzene, having the structure of formula (II)

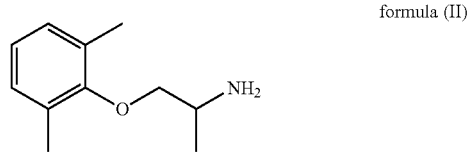

formula (II)

and any prodrug, pharmaceutically acceptable salt, hydrate, solvate, or combination thereof, including but not limited to mexiletine hydrochloride.

Mexiletine is a sodium channel blocker that has been used for the treatment of documented ventricular arrhythmias, such as sustained ventricular tachycardia since early 1970s.[13,14] It also blocks $I_{NA-L}$, which has recently been shown to be an effective treatment approach to terminate TdP in acquired LQTS, such as LQTS acquired by the administration of dofetilide.[11] However, it is generally believed that mexiletine exerts little electrophysiological effect in atria, i.e. that it is not atria-selective. Therefore, mexiletine is not indicated for effective treatment of atrial fibrillation,[15] and it is also not included in any of the guidelines for the management of patients with atrial fibrillation by American College of Cardiology, American Heart Association and the Heart Rhythm Society.[16]

Two major benefits of the invention include an enhanced efficacy in the prevention and termination of atrial fibrillation and marked reduction of the risk for the life-threatening arrhythmia TdP.

It is surprisingly shown in the invention that the administration of an effective amount of dofetilide and an effective amount of mexiletine not only resulted in marked reduction of adverse effects, but also significant improvement in the efficacy, as compared to the conventional atrial fibrillation treatment by dofetilide alone. For example, it was observed that a method according to an embodiment of the invention resulted in reduced risk for the life-threatening arrhythmia TdP, as well as synergistic increase in atrial ERP and suppression of induced atrial fibrillation.

While not wishing to be bound by theory, it is believed that due to the differences in $I_{NA-L}$ current densities between the atria and ventricles,[10] mexiletine has a preferential inhibitory effect on ventricular repolarization. Increased $I_{NA-L}$ current, which may occur under conditions like hypokalemia, ventricular hypertrophy, heart failure, and myocardial ischemia, can further potentiate the QT prolonging effect of dofetilide, leading to the life-threatening arrhythmia TdP. It was discovered that mexiletine not only reduces QT interval prolongation mildly, but also reduces the risk of TdP significantly even at the same QT prolongation.[11] It is also believed that that the synergistic effect of dofetilide and mexiletine on suppression of atrial fibrillation is related to prolongation of atrial action potential duration by dofetilide, which amplify $I_{NA-L}$ current that is different from fast sodium current ($I_{NA-S}$), and therefore increases binding of mexiletine to sodium channels during action potential and such an increased binding can further prolong ERP by dofetilide. In other words, mexiletine significantly shifts preferential electrophysiological effect of dofetilide on ventricles (for example QT prolongation and TdP) to atria (i.e. increase in atrial ERP and suppression of atrial fibrillation). This results in an increased efficacy of dofetilide in the treatment of atrial fibrillation with a reduced risk for ventricular proarrhythmias.

The invention makes it possible to use a smaller dose of dofetilide, which, when used in combination with mexiletine, to achieve the same level of treatment efficacy as that obtained from a larger dose of dofetilide without mexiletine. On the other hand, for patients with atrial fibrillation refractory to radiofrequency ablation and currently available antiarrhythmic drugs, the dofetilide and mexiletine doses can be titrated up for better control of atrial fibrillation because combined use of the two drugs exhibits a significantly improved safety profile. Accordingly, by combining mexiletine with dofetilide, one can now use a wider dosage range than that of the conventional treatment with dofetilide alone to provide safer and more effective treatment of atrial fibrillation to a larger patient population in need of such treatment.

In one general aspect, embodiments of the invention relate to a pharmaceutical composition for treating atrial fibrillation or a symptom associated therewith in a subject, which comprises an effective amount of dofetilide, an effective amount of mexiletine, and a pharmaceutically acceptable carrier. The pharmaceutical compositions can be presented in any form suitable for the invention, and prepared by any of the methods known in the art of pharmacy in view of the present disclosure.

Preferably, pharmaceutical compositions according to embodiments of the invention are formulated for oral administration. Pharmaceutical compositions adapted for oral administration include solid forms such as pills, tablets, caplets, and hard or soft capsules (each including immediate release, timed release, and sustained release formulations) as well as lozenges and dispersible powders or granules. Liquid forms of pharmaceutical compositions adapted for oral administration include solutions, syrups, elixirs, emulsions, and aqueous or oily suspensions. Any of these dosage forms may be prepared according to any method or compounding technique known in the art for the manufacture of pharmaceutical compositions. Pharmaceutically acceptable carriers that may be desirably utilized in the manufacture of solid oral dosage forms include inert diluents, such as calcium carbonate, sodium carbonate, lactose, calcium phosphate or sodium phosphate; granulating or disintegrating agents, such as corn starch or alginic acid; binding agents, such as starch, gelatin, or acacia; and lubricating agents such as magnesium stearate, stearic acid or talc. If desired, solid pharmaceutical compositions adapted for oral administration may further include one or more sweetening agents, flavoring agents, coloring agents, or preserving agents in order to provide attractive or palatable preparations.

In those embodiments wherein the dosage form is a tablet or pill, it may either be uncoated or coated, and if coated, may be coated by any known technique. Further, the coating, if desirably provided, can be formulated or applied by known techniques so that the coating can delay disintegration of the tablet or pill, and thus, absorption of the active ingredient, thereby providing a controlled and/or sustained release dosage form capable of providing sustained therapeutic or prophylactic effect over a longer period. For example, the tablet or pill can comprise an inner dosage and an outer dosage component, the latter being in the form of an envelope over the former. An enteric layer that serves to resist disintegration in the stomach and permits the inner component to pass substantially intact into the duodenum or to be delayed in release can separate the two components. A variety of materials can be used for such enteric layers or coatings, including a number of polymeric acids, shellac, acetyl alcohol and cellulose acetate. Alternatively, in those embodiments wherein such a controlled and or sustained release is desired, tablets, pills or capsules may be formulated as osmotic pump dosage forms by any known method.

Pharmaceutical compositions adapted for oral administration may also be presented as hard or soft gelatin capsules, wherein the active ingredient may be mixed with an inert solid diluent, such as calcium carbonate, calcium phosphate or kaolin in the case of the former or with water or miscible solvents such as propylene glycol, PEG's and ethanol, or an oil medium such as peanut oil, liquid paraffin, or olive oil in the case of the latter.

Aqueous suspensions can be prepared that contain the active ingredient(s) in admixture with excipients suitable for the manufacture of aqueous suspensions. Such excipients include suspending agents, such as sodium carboxymethylcellulose, methylcellulose, hydroxypropylmethylcellulose, sodium alginate, polyvinyl-pyrrolidone, gum tragacanth and gum acacia, dextran, polyvinyl-pyrrolidone or gelatin; and dispersing or wetting agents such as lecithin, polyoxyethylene stearate, heptadecaethyleneoxycetanol, polyoxyethylene sorbitol monooleate, and polyethylene sorbitan monooleate. Aqueous suspensions may also contain one or more preservatives, such as ethyl or n-propyl, p-hydroxybenzoate; one or more coloring agents, one or more flavoring agents, and one or more sweetening agents, such as sucrose, saccharine or aspartame.

Oily suspensions may be formulated by suspending the active ingredient(s) in a vegetable oil, such as cottonseed, olive, sesame or coconut oil, or in a mineral oil, such as liquid paraffin. The oily suspensions may contain a thickening agent, such as beeswax, hard paraffin, or acetyl alcohol. Sweetening agents such as those set forth above, and flavoring agents may be added to provide a palatable oral preparation. Such oily suspensions may be preserved by the inclusion of an anti-oxidant such as ascorbic acid.

Dispersible powders and granules suitable for the preparation of an aqueous suspension suitable for oral administration can provide the active ingredient(s) in admixture with a dispersing or wetting agent, suspending agent, and one or more preservatives, all of which have been discussed above. Sweetening, flavoring, or coloring agents may also be present, if desired.

Pharmaceutical compositions suitable for oral administration may also be presented in the form of an oil-in-water emulsion. The oily phase may be a vegetable or mineral oil, such as those described above, or mixtures of these. Suitable emulsifying agents may be naturally-occurring phosphatides, such as soy bean, lecithin, sorbitan monooleate, or polyoxyethylene sorbitan monooleate. The emulsions may also contain sweetening or flavoring agents.

Syrups and elixirs may be formulated with sweetening agents, for example, glycerol, propylene glycol, sorbitol or sucrose. Such formulations may also contain a demulcent, a preservative and flavoring or coloring agents.

In another embodiment, pharmaceutical compositions of the invention are provided in a form adapted for parenteral administration, e.g., by injection or infusion. For example, the pharmaceutical compositions can be formulated for intravenous, intra-arterial, intra-muscular or subcutaneous injection. Injectable aqueous or oleaginous suspensions are desirably sterile and can be formulated according to known methods using suitable dispersing, wetting and suspending agents as mentioned above. A parenterally-acceptable diluent or solvent can also be utilized, such as 1,3-butanediol, water, Ringer's solution, and isotonic sodium chloride. Cosolvents such as ethanol, propylene glycol or polyethylene glycols may also be used. In addition, sterile, fixed oils are conventionally employed as solvents or suspending mediums in injectable or infusible solutions, and these may include any bland fixed oil, such as any of the synthetic mono- or diglycerides. Fatty acids such as oleic acid also may be utilized in the preparation of injectable or infusible solutions.

Active ingredients according to embodiments of the invention can also be provided in a pharmaceutical composition in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The effective amount of therapeutically active ingredients to be included in a dosage form will depend upon factors, such as the patient being treated, the mode of administration and the desired delivered dose. Representative pharmaceutical compositions can generally include 50 mcg to 2500 mcg of dofetilide, and 30 mg to 600 mg of mexiletine per dosage form. The effective amount of mexiletine can also be 50 mg to 450 mg or 100 mg to 300 mg per dosage form. Examples of the effective amount of mexiletine can include, but are not limited to, 30 mg, 50 mg, 80 mg, 100 mg, 200 mg, 250 mg, 300 mg, 350 mg, 400 mg, 450 mg, 500 mg, 550 mg or 600 mg per dosage form.

In one embodiment of the invention, a pharmaceutical composition comprises an effective amount of mexiletine, such as that described herein, a pharmaceutically acceptable carrier, and an effective amount of dofetilide that is lower than that used for the conventional dofetilide treatment. For example, the pharmaceutical composition can include 50 mcg to 100 mcg, such as 50 mcg, 75 mcg or 100 mcg, of dofetilide per dosage form. Such pharmaceutical composition can be particularly useful for treating patients who are prone or sensitive to the risk of adverse effects induced by dofetilide.

In another embodiment of the invention, a pharmaceutical composition comprises an effective amount of mexiletine, such as that described herein, a pharmaceutically acceptable carrier, and an effective amount of dofetilide that is within the range used for the conventional dofetilide treatment. For example, the pharmaceutical composition can include 125 mcg to 500 mcg, such as 25 mcg, 150 mcg, 200 mcg, 225 mcg, 250 mcg, 275 mcg, 300 mcg, 400 mcg or 500 mcg, of dofetilide per dosage form. Such pharmaceutical composition can provide more effective treatment of atrial fibrillation or a symptom associated therewith with less adverse effects than the conventional treatment.

In yet another embodiment of the invention, a pharmaceutical composition comprises an effective amount of mexiletine, such as that described herein, a pharmaceutically acceptable carrier, and an effective amount of dofetilide that is higher than that used for the conventional dofetilide treatment. For example, the pharmaceutical composition can include 525 mcg to 2500 mcg, such as 525 mcg, 550 mcg, 600 mcg, 700 mcg, 800 mcg, 900 mcg, 1000 mcg, 1250 mcg, 1500 mcg, 1750 mcg, 2000 mcg, 2250 mcg, or 2500 mcg, of dofetilide per dosage form. Such pharmaceutical composition is particularly useful for treating patients with atrial fibrillation refractory to radiofrequency ablation and currently available antiarrhythmic drugs.

In a preferred embodiment of the invention, a pharmaceutical composition comprises 200 mcg to 1000 mcg dofetilide and 100 mg to 500 mg mexiletine hydrochloride per dosage form, more preferably, per capsule. For example, the pharmaceutical composition, such as a capsule, can comprise 200-500 mcg, 505-600 mcg, 605-700 mcg, 705-800 mcg, 805-900 mcg, or 905-1000 mcg dofetilide and 100 mg, 200 mcg, 300 mcg, 400 mcg or 500 mg mexiletine, and a pharmaceutically acceptable carrier.

A pharmaceutical composition according to an embodiment of the present invention can optionally comprise one or more other therapeutically active ingredients, such as another class of antiarrhythmic agent or another selective $I_{NA-L}$ inhibitor.

In another general aspect, the invention relates to a method of treating atrial fibrillation or a symptom associated therewith in a subject in need thereof. The method comprises administering to the subject an effective amount of dofetilide and an effective amount of mexiletine.

According to embodiments of the invention, a method of the invention results in reduced adverse effects, such as adverse cardiovascular effects (including tachycardia, bradycardia, LQTS, TdP, cardiomyopathy), hypothyroidism, edema of the extremities, headache, dizziness, flushing, fatigue, vertigo, muscle cramps, hallucination, diarrhea, fever, urinary retention, vomiting, body rash/itching, etc.

In one embodiment of the invention, the dofetilide and the mexiletine are administered to a subject in need thereof in a single pharmaceutical composition, such as that described herein.

In another embodiment of the invention, the dofetilide and the mexiletine are administered to a subject in need thereof separately in separate pharmaceutical compositions. The two drugs can be administered in any order, at approximately the same time. The two drugs can also be administered at different time points with mexiletine first followed by dofetilide, so long as the dosing schedules of dofetilide and mexiletine overlap, such that the administered mexiletine is effective to reduce the risk of adverse effects, including but not limited to, QT prolongation, associated with the administered dofetilide, and/or to enhance the efficacy of the administered dofetilide.

The methods according to embodiments of the present invention can optionally comprise administering to the subject other therapeutically active ingredients, such as another class of antiarrhythmic agent or another $I_{NA-L}$ inhibitor, or in combination with other treatments, such as radiofrequency ablation.

Whether administered alone or in combination with an additional therapeutic agent, the therapeutic active ingredients can be administered by any known suitable route of administration. Preferably, the therapeutic active ingredients are administered orally, or parenterally (including subcutaneous, intravenous, intramuscular, and intrasternal injection or infusion administration techniques) in dosage units or pharmaceutical compositions containing conventional pharmaceutically acceptable carriers and any such dosage units or pharmaceutical compositions are within the scope of the invention.

The effective amounts of therapeutically active ingredients to be administered to a subject in need thereof will depend upon factors, such as the subject being treated, the mode of administration and the desired delivered dose. For example, an effective amount of 50 mcg to 2500 mcg of dofetilide and an effective amount of 30 mg to 600 mg of mexiletine can be administered per administration. The effective amount of mexiletine can also be 50 mg to 450 mg or 100 mg to 300 mg per administration. Examples of the effective amount of mexiletine include, but are not limited to, 30 mg, 50 mg, 80 mg, 100 mg, 200 mg, 250 mg, 300 mg, 350 mg, 400 mg, 450 mg, 500 mg, 550 mg or 600 mg per administration.

In one embodiment of the invention, a method of the invention comprises administering to a subject in need thereof an effective amount of mexiletine, such as that described herein, and an effective amount of dofetilide that is lower than that used for the conventional dofetilide treatment. For example, the effective amount of dofetilide can be 50 mcg to 100 mcg, such as 50 mcg, 75 mcg or 100 mcg, of dofetilide per administration. Such method can be particularly useful for patients who are prone or sensitive to the risk of adverse effects induced by dofetilide.

In another embodiment of the invention, a method of the invention comprises administering to a subject in need thereof an effective amount of mexiletine, such as that described herein, and an effective amount of dofetilide that is within the range used for the conventional dofetilide treatment. For example, the effective amount of dofetilide can be 125 mcg to 500 mcg, such as 25 mcg, 150 mcg, 200 mcg, 225 mcg, 250 mcg, 275 mcg, 300 mcg, 400 mcg or 500 mcg, of dofetilide per administration. Such method can provide more effective treatment with less adverse effects than the conventional treatment.

In yet another embodiment of the invention, a method of the invention comprises administering to a subject in need thereof an effective amount of mexiletine, such as that described herein, and an effective amount of dofetilide that is higher than that used for the conventional dofetilide treatment. For example, the effective amount of dofetilide can be 525 mcg to 2500 mcg, such as 525 mcg, 550 mcg, 600 mcg, 700 mcg, 800 mcg, 900 mcg, 1000 mcg, 1250 mcg, 1500 mcg, 1750 mcg, 2000 mcg, 2250 mcg, or 2500 mcg, of dofetilide per administration. Such method is particularly useful for treating patients with atrial fibrillation refractory to radiofrequency ablation and currently available antiarrhythmic drugs.

The effective amounts of therapeutically active ingredients can be administered once or multiple times to a subject in need thereof. For example, the effective amounts of therapeutically active ingredients can be administered to the subject once or twice daily depending on the need.

In a preferred embodiment of the invention, a method of treating atrial fibrillation or a symptom associated therewith in a subject in need thereof comprising administering to the subject 200 mcg to 1000 mcg dofetilide and 100 mg to 500 mg mexiletine hydrochloride, more preferably, the dofetilide and mexiletine hydrochloride are present in one or more capsules. For example, the method can comprise administering to a subject in need thereof a pharmaceutical composition, such as a capsule, comprising 200-500 mcg, 505-600 mcg, 605-700 mcg, 705-800 mcg, 805-900 mcg, or 905-1000 mcg dofetilide, and 100 mg, 200 mcg, 300 mcg, 400 mcg or 500 mg mexiletine, and a pharmaceutically acceptable carrier. The method can also comprise administering to a subject in need thereof a first pharmaceutical composition, such as a capsule, comprising 100 mg, 200 mcg, 300 mcg, 400 mcg or 500 mg mexiletine, and a pharmaceutically acceptable carrier, and a second pharmaceutical composition, such as a capsule, comprising 200-500 mcg, 505-600 mcg, 605-700 mcg, 705-800 mcg, 805-900 mcg, or 905-1000 mcg dofetilide, and a pharmaceutically acceptable carrier. The first and second pharmaceutical compositions can be administered at about the same time in any order, or at different time points with the first pharmaceutical composition being administered first, followed by the administration of the second pharmaceutical composition.

According to embodiments of the invention, the administration of the effective amount of mexiletine and the effective amount of dofetilide significantly increases atrial effective refractory period (ERP) in comparison to that achieved by the administration of the effective amount of dofetilide alone, and reduces at least one of early afterdepolarization (EAD), EAD-dependent R-on-T extrasystoles, and Torsades de Pointes (TdP) induced by the administration of the effective amount of dofetilide in the subject.

Another general aspect of the invention relates to a method of manufacturing a pharmaceutical composition. The method comprises combining an effective amount of dofetilide, an effective amount of mexiletine, and a pharmaceutically acceptable carrier to obtain the pharmaceutical composition. Any suitable method known to those skilled in the art can be used to manufacture a pharmaceutical composition of the invention in view of the present disclosure. In general, the pharmaceutical compositions are prepared by uniformly and intimately admixing the active ingredients with liquid carriers or finely divided solid carriers or both, and then, if necessary, shaping the product into the desired presentation.

This invention will be better understood by reference to the non-limiting example that follows, but those skilled in the art will readily appreciate that the example is only illustrative of the invention as described more fully in the claims which follow thereafter.

EXAMPLE

Arterially Perfused Rabbit Atrial Wedge Preparations and Electrophysiologic Recordings Animal research data demonstrate that use of dofetilide with mexiletine, a drug that blocks cardiac sodium current, can significantly increase the effective refractory period (ERP) in rabbit atrial tissue. ERP is a most important parameter in cardiac electrophysiology that determines vulnerability of cardiac tissues for the development of arrhythmias including atrial fibrillation. A longer ERP results in better treatment and prevention of cardiac arrhythmias. The synergistic effect of dofetilide and mexiletine on atrial ERP can more effectively suppress atrial fibrillation than dofetilide alone. Additionally, mexiletine, due to its inhibitory effect on late sodium current, can significantly reduce the risk of TdP associated with dofetilide treatment based on recent studies,[11] the entire content of which is incorporated herein by reference.

Materials and Method

Rabbits (New Zealand White) of either sex, weighing 2.0-2.8 kg were injected with heparin (800 U/kg) via an ear vein and anesthetized by intramuscular injection of xylazine (5 mg/kg) and intravenous administration of ketamine HCl (30-35 mg/kg, i.v.). The chest was opened via a left thoracotomy, and the heart was excised and placed in a cardioplegic solution consisting of cold (4° C.) normal Tyrode's solution.

Surgical preparation of the rabbit right or left atrial wedge was essentially similar to that in *Preclinical assessment of drug-induced proarrhythmias: role of the arterially perfused rabbit left ventricular wedge preparation*,[18] herein incorporated by reference. Briefly, the atrial preparation was dissected from the rabbit heart and cannulated via a coronary artery branch, either from the right coronary artery (the right atrial wedge) or the left coronary artery (the left atrial wedge), and perfused with a cardioplegic solution. Similarly, the left ventricular wedge preparation was dissected from the rabbit heart and arterially cannulated via a branch of left coronary artery. The atrial or ventricular wedge preparation was then placed in a small tissue bath and arterially perfused with Tyrode's solution containing 4.0 mM $K^+$ buffered with 95% $O_2$ and 5% $CO_2$ at a temperature of 35.7±0.1° C. The preparations were paced at basic cycle lengths (BCL) of 300, 500, 1000 and 2000 ms.

Two extracellular silver/silver chloride electrodes were placed on the endocardial or epicardial surfaces to record bipolar atrial electrograms (EGM). A transmural ECG was recorded in the ventricular wedge preparation using two extracellular silver/silver chloride electrodes placed in the bath 0.5 to 1.5 cm from the epicardial and endocardial surfaces of the preparation (Epi: "+" pole). Transmembrane action potential was recorded from the endocardium or epicardium using the floating glass microelectrodes. Atrial action potential duration at 90% repolarization ($APD_{90}$) was used for data analysis.

Atrial effective refractory period (ERP) was measured by introducing an extrastimulus (S2) repeatedly every 10 pulses (S1) at two folds of the pacing threshold. ERP was defined as the longest S1-S2 interval that failed to capture the atrial wedge preparation. In the preparations that lost excitation intermittently after drug interventions, the ERP was then considered to be equal to the S1-S1 interval.

Atrial fibrillation was induced by programming stimulation using single or double extrastimuli (S2 and S3). Basic cycle lengths (S1 and S1) of 1000 and 500 ms were used for induction of atrial fibrillation.

Early afterdepolarization (EAD), EAD-dependent R-on-T extrasystoles and torsade de pointes (TdP) were induced by dofetilide in the rabbit left ventricular wedges which were paced at a BCL of 2000 ms and perfused with Tyrode's solution containing 3 mM $K^+$, which is equivalent to hypokalemia in humans. Lower $K^+$ potentiated the effect of dofetilide to induced EAD, R-on-T and TdP. The $K^+$ concentration in Tyrode's solution remained the same when the effect of mexiletine on dofetilide-induced EAD, R-on-T and TdP was examined.

Data Analysis

Data were expressed as Mean±Standard Error of the Mean (SEM). Student's T test was used to determine the statistical significance of differences between control and test conditions. Chi-Square analysis was used to compare statistical difference in incidences between control and test conditions. Significance was defined as a value of $p<0.05$.

Figure 1:
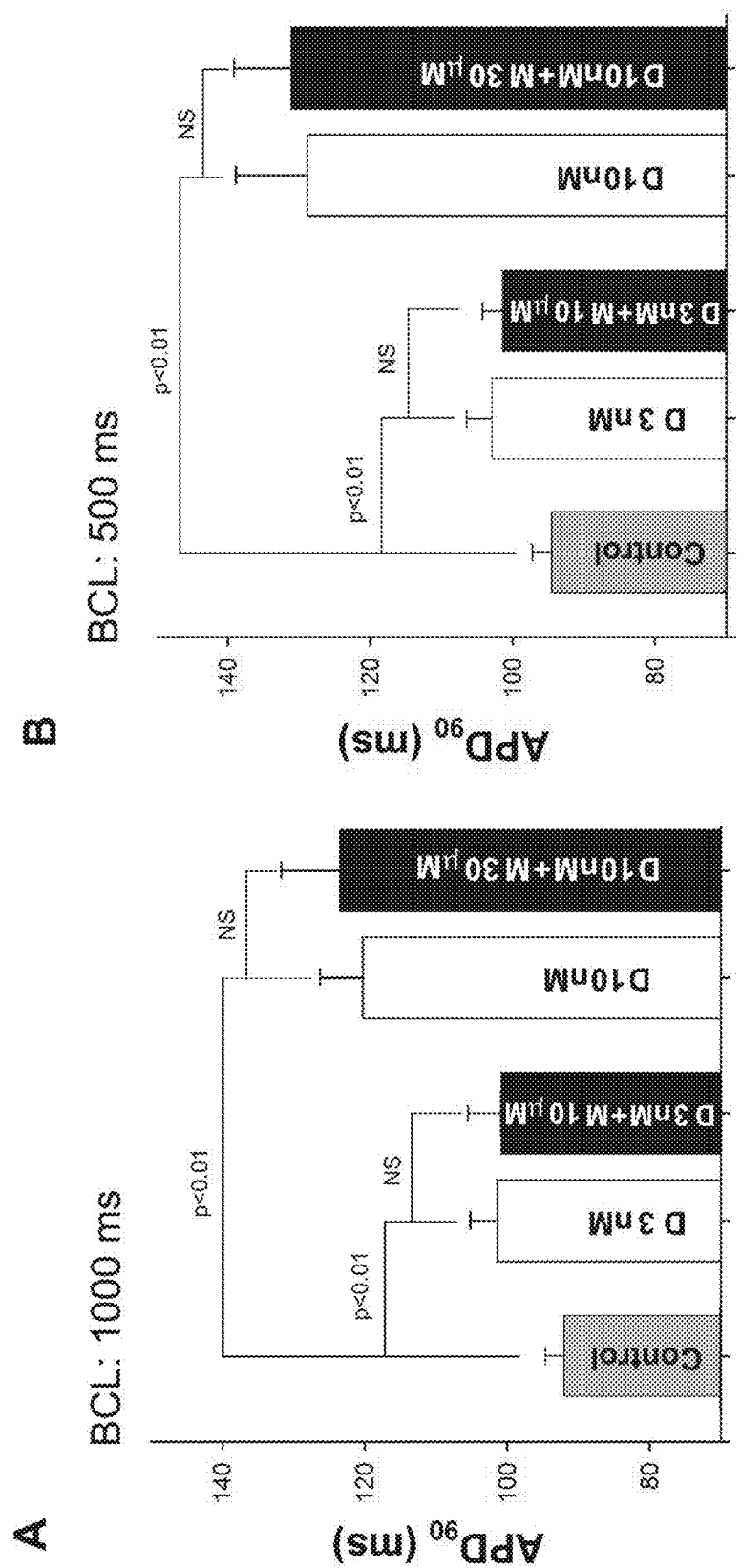

Results—Combined Use of Dofetilide and Mexiletine on the Rabbit Atrial APD and ERP FIG. 1 shows the effect of dofetilide (D) and dofetilide plus mexiletine (M) on atrial APD in rabbit. As shown in the data, dofetilide (3 nM and 10 nM) significantly increased atrial $APD_{90}$, and the addition of mexiletine (10 μM and 30 μM) exhibited no significant additional effect on prolonged atrial $APD_{90}$ by dofetilide.

Figure 2:
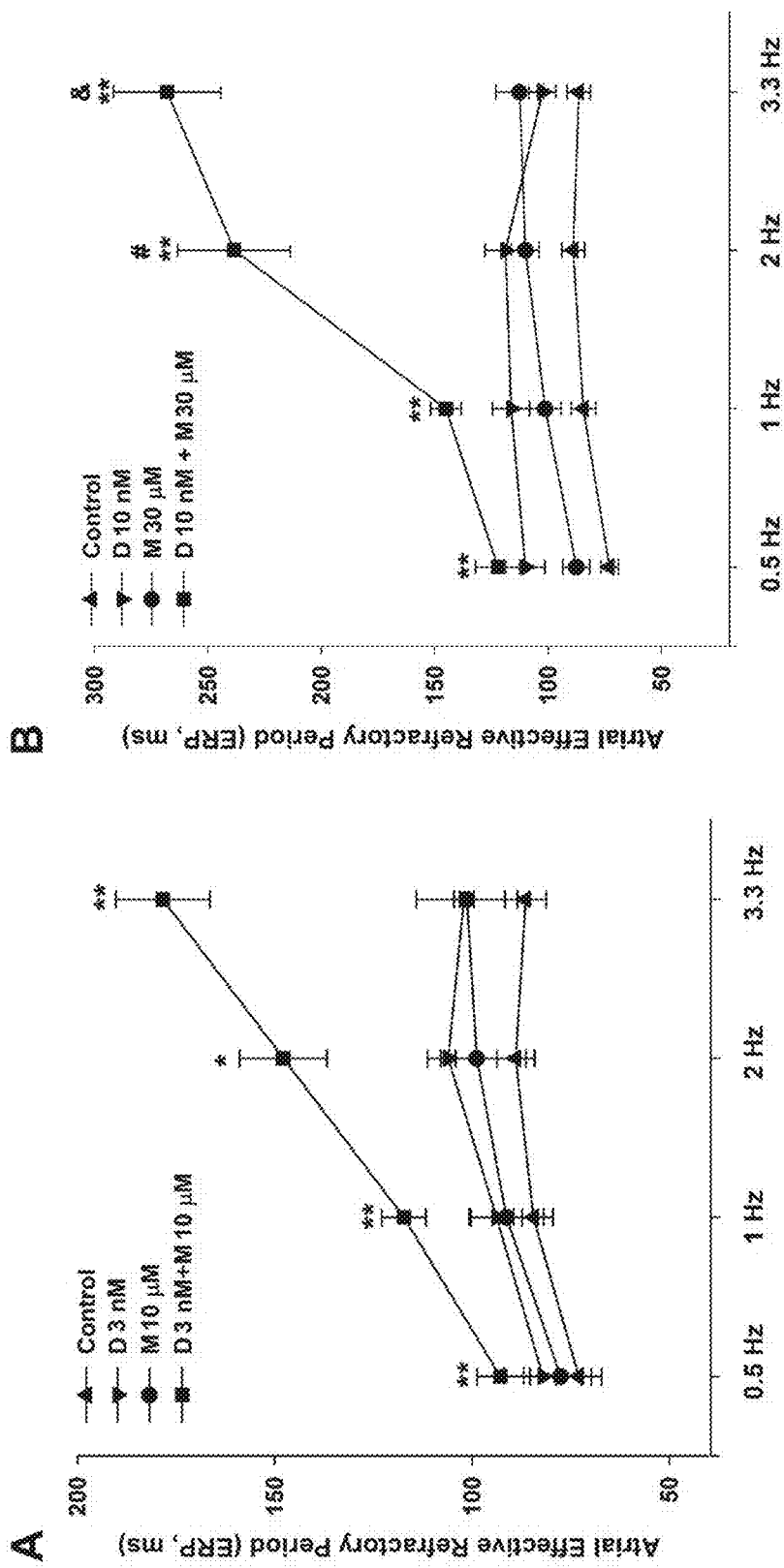
Figure 3:
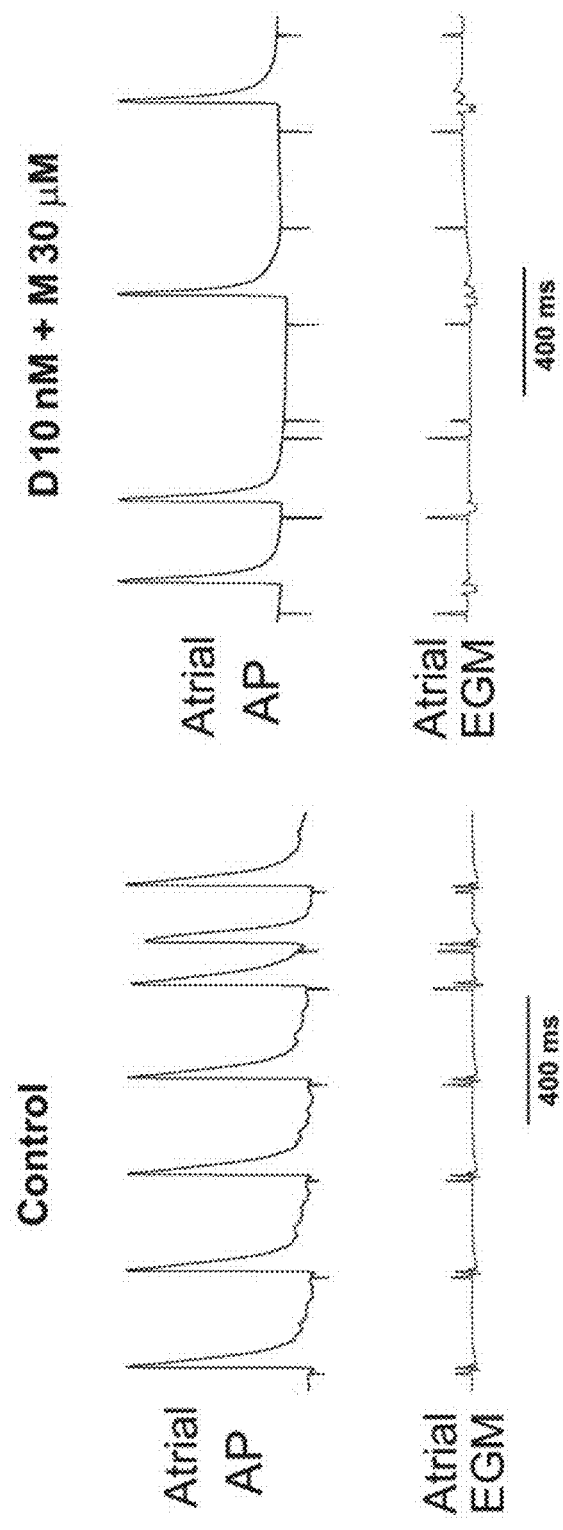
FIG. 3 illustrates, by way of atrial pacing and electrogram readings, that dofetilide (D) plus mexiletine (M) at relative higher concentrations (10 nM and 30 µM, respectively) caused intermittent loss of excitation at the pacing rate of 3.3 Hz, wherein AP refers to action potential, and EGM refers to electrogram.

Although each of dofetilide and mexiletine mildly to moderately prolonged atrial ERP, combined use of dofetilide and mexiletine markedly increased atrial ERP, particularly during fast pacing rates (FIG. 2). Dofetilide at 3 nM and mexiletine at 10 μM are close to the respective therapeutical plasma concentrations of dofetilide and mexiletine in humans.[19-21] At these concentrations, dofetilide plus mexiletine increased the atrial ERP by 28.2% from 72.2±5.7 ms to 92.8±5.9 ms (n=9, p<0.01) at a pacing rate of 0.5 Hz (i.e. BCL: 2000 ms), by 39.7% from 83.9±5.0 ms to 117.2±5.6 ms (n=9, p<0.01) at 1 Hz, by 60.2% from 92.2±4.7 ms to 147.8±11.1 ms (n=9, p<0.05) at 2 Hz, and by 94.5% from 91.7±5.2 ms to 178.3±12.0 ms (n=9, p<0.01) at 3.3 Hz. With combined use of dofetilide and mexiletine at relatively higher concentrations of 10 nM and 30 μM respectively, there was intermittent loss of excitation in 4 of 7 atrial wedge preparations at a pacing rate of 3.3 Hz (FIG. 3). This indicates that the increase in ERP may be underestimated at 3.3 Hz (FIG. 2, right panel). At these relatively higher concentrations, none of the atrial preparations lost excitation when dofetilide or mexiletine was used alone.

Figure 4:
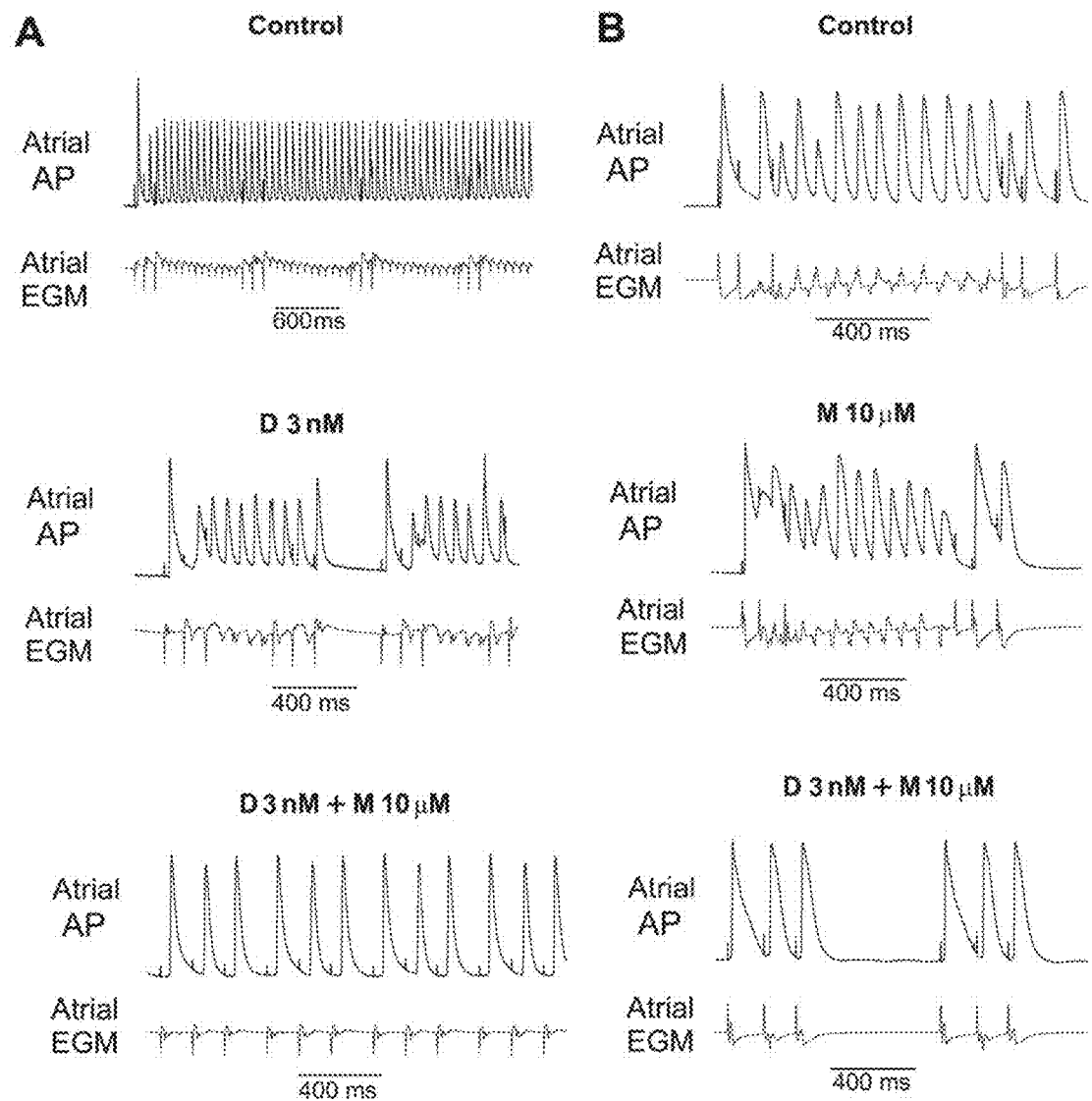
FIG. 4 illustrates, by way of atrial pacing and electrogram readings, the effect of dofetilide (D), mexiletine (M) and D plus M on induction of atrial fibrillation by programming stimulation, wherein AP refers to action potential; and EGM refers to electrogram.

As shown in FIG. 4, atrial fibrillation could be induced by programming stimulation. Induction of atrial fibrillation could be partially suppressed by dofetilide alone but not mexiletine alone (Table 1). Induction of atrial fibrillation was completely suppressed by combined use of dofetilide and mexiletine.

TABLE 1

Effects of dofetilide plus mexiletine of the incidence of atrial fibrillation in arterially-perfused rabbit atrial wedge preparations

| | Induced Atrial Fibrillation | |
|---|---|---|
| Control (C) | 10 of 10 preparations | |
| Dofetilide (D) 3 nM | 3 of 6 preparations | p < 0.05 compared with C, and D + M |
| Mexiletine (M) 10 μM | 4 of 4 preparations | p < 0.01 compared with D + M, NS compared with C |
| D 3 nM + M 10 μM | 0 of 10 preparations | |

In an atrial wedge preparation, non-sustained atrial fibrillation could be readily induced by programming stimulation with only single stimuli. As shown in FIG. 5, dofetilide (D) at relatively higher concentrations (10 nM and 30 nM) alone reduced only duration and incidences of atrial fibrillation. Dofetilide plus mexiletine (M), at 10 nM and 30 μM, respectively, completely suppressed induction of atrial fibrillation. The effect of dofetilide plus mexiletine on atrial fibrillation could be partially washable.

As shown in FIG. 6, mexiletine (10 μM) effectively abolished EAD, R-on-T and TdP induced by 10 nM dofetilide in the rabbit left ventricular wedge preparation perfused with low (3 mM) K$^+$ (see also Table 2). The effect of mexiletine on dofetilide-induced EAD, R-on-T and TdP is washable: after removal of mexiletine, EAD, R-on-T reoccurred.

TABLE 2

Effects of mexiletine (M) on dofetilide (D)-induced early afterdepolarization (EAD), EAD-dependent R-on-T extrasystoles and torsade de pointes (TdP) in arterially-perfused rabbit left ventricular wedge preparations

|  | EAD | R-on-T | TdP |
| --- | --- | --- | --- |
| Control (C) | 0 of 7 | 0 of 7 | 0 of 7 |
| D 10 nM | 7 of 7 | 5 of 7 | 1 of 7 |
| D 10 nM + M 10 μM | 0 of 7** | 0 of 7** | 0 of 7 |

**p < 0.01.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

REFERENCES

1. Guo Y, Tian Y, Wang H, Si Q, Wang Y, Lip G Y. Prevalence, incidence, and lifetime risk of atrial fibrillation in China: new insights into the global burden of atrial fibrillation. *Chest* 2015; 147: 109-119.
2. Chei C L, Raman P, Ching C K, Yin Z X, Shi X M, Zeng Y, Matchar D B. Prevalence and Risk Factors of Atrial Fibrillation in Chinese Elderly: Results from the Chinese Longitudinal Healthy Longevity Survey. *Chin Med J (Engl)* 2015; 128: 2426-2432.
3. Chugh S S, Havmoeller R, Narayanan K, Singh D, Rienstra M, Benjamin E J, Gillum R F, Kim Y H, McAnulty J H, Jr., Zheng Z J, Forouzanfar M H, Naghavi M, Mensah G A, Ezzati M, Murray C J. Worldwide epidemiology of atrial fibrillation: a Global Burden of Disease 2010 Study. *Circulation* 2014; 129: 837-847.
4. Colilla S, Crow A, Petkun W, Singer D E, Simon T, Liu X. Estimates of current and future incidence and prevalence of atrial fibrillation in the U.S. adult population. *Am J Cardiol* 2013; 112: 1142-1147.
5. Suttorp M J, Polak P E, van 't H A, Rasmussen H S, Dunselman P H, Kingma J H. Efficacy and safety of a new selective class III antiarrhythmic agent dofetilide in paroxysmal atrial fibrillation or atrial flutter. *Am J Cardiol* 1992; 69: 417-419.
6. Rasmussen H S, Allen M J, Blackburn K J, Butrous G S, Dalrymple H W. Dofetilide, a novel class III antiarrhythmic agent. *J Cardiovasc Pharmacol* 1992; 20 Suppl 2: S96-105.
7. Zimetbaum P. Antiarrhythmic drug therapy for atrial fibrillation. *Circulation* 2012; 125: 381-389.
8. Qin D, Leef G, Alam M B, Rattan R, Munir M B, Patel D, Khattak F, Adelstein E, Jain S K, Saba S. Comparative effectiveness of antiarrhythmic drugs for rhythm control of atrial fibrillation. *J Cardiol* 2015.
9. Aktas M K, Shah A H, Akiyama T. Dofetilide-induced long QT and torsades de pointes. *Ann Noninvasive Electrocardiol* 2007; 12: 197-202.
10. Qi D, Yang Z, Robinson V M, Li J, Gao C, Guo D, Kowey P R, Yan G X. Heterogeneous distribution of INa-L determines interregional differences in rate adaptation of repolarization. *Heart Rhythm* 2015; 12: 1295-1303.
11. Badri M, Patel A, Patel C, Liu G, Goldstein M, Robinson V M, Li J, Xue X, Yang L, Kowey P R, Yan G X. Mexiletine Prevents Recurrent Torsades de Pointes in Acquired Long QT Syndrome Refractory to Conventional Measures. *JACC: Clinical Electrophysiology* 2015; 1: 315-322.
12. Yan G X, Wu Y, Liu T, Wang J, Marinchak R A, Kowey P R. Phase 2 early afterdepolarization as a trigger of polymorphic ventricular tachycardia in acquired long-QT syndrome: direct evidence from intracellular recordings in the intact left ventricular wall. *Circulation* 2001; 103: 2851-2856.
13. Talbot R G, Nimmo J, Julian D G, Clark R A, Neilson J M, Prescott L F. Treatment of ventricular arrhythmias with mexiletine (Ko 1173). *Lancet* 1973; 2: 399-404.
14. Campbell N P, Kelly J G, Shanks R G, Chaturvedi N C, Strong J E, Pantridge J F. Mexiletine (Ko 1173) in the management of ventricular dysrhythmias. *Lancet* 1973; 2: 404-407.
15. Miller J M, Zipes D P. Therapy for Cardiac Arrhythmias. In: Mann D. L., Zipes D. P., Libby P., Bonow J. O. (eds) Braunwald's Heart Disease: A Textbook of Cardiovascular Medicine. Elsevier Publisher. 2014: 693.
16. January C T, Wann L S, Alpert J S, Calkins H, Cigarroa J E, Cleveland J C, Jr., Conti J B, Ellinor P T, Ezekowitz M D, Field M E, Murray K T, Sacco R L, Stevenson W G, Tchou P J, Tracy C M, Yancy C W. 2014 AHA/ACC/HRS guideline for the management of patients with atrial fibrillation: executive summary: a report of the American College of Cardiology/American Heart Association Task Force on practice guidelines and the Heart Rhythm Society. *Circulation* 2014; 130: 2071-2104.
17. Yan G X, Antzelevitch C. Cellular basis for the electrocardiographic J wave. *Circulation* 1996; 93: 372-379.
18. Wang D, Patel C, Cui C, Yan G X. Preclinical assessment of drug-induced proarrhythmias: role of the arterially perfused rabbit left ventricular wedge preparation. *Pharmacol Ther* 2008; 119: 141-151.
19. Ono K, Kiyosue T, Arita M. Comparison of the inhibitory effects of mexiletine and lidocaine on the calcium current of single ventricular cells. *Life Sci* 1986; 39: 1465-1470.
20. Gottlieb S S, Weinberg M. Cardiodepressant effects of mexiletine in patients with severe left ventricular dysfunction. *Eur Heart J* 1992; 13: 22-27.
21. http://www.accessdata.fda.gov/drugsatfda_docs/nda/99/20-931_Tikosyn_admindocs_P2.pdf

What is claimed is:

1. A pharmaceutical composition for treating or preventing atrial fibrillation or a symptom associated therewith in a subject in need thereof, comprising: (a) an effective amount of dofetilide, (b) an effective amount of mexiletine, and (c) a pharmaceutically acceptable carrier, wherein the effective amount of dofetilide is 50 mcg to 2500 mcg, and the effective amount of mexiletine is 30 mg to 600 mg.

2. The pharmaceutical composition of claim 1 wherein the mexiletine is mexiletine hydrochloride.

3. The pharmaceutical composition of claim 1 comprising 50 mcg to 2500 mcg dofetilide and 30 mg to 600 mg mexiletine per dosage form.

4. The pharmaceutical composition of claim 1, further comprising one or more other therapeutically active ingredients.

5. The pharmaceutical composition of claim 1 formulated to be administered orally.

6. The pharmaceutical composition of claim 5 being a capsule, comprising 200 mcg to 1000 mcg dofetilide and 100 mg to 500 mg mexiletine hydrochloride.

7. The pharmaceutical composition of claim 1 formulated to be administered parenterally.

8. A method of treating or preventing atrial fibrillation or a symptom associated therewith in a subject in need thereof, the method comprising administering to the subject the pharmaceutical composition of claim 1.

9. A method of treating or preventing atrial fibrillation or a symptom associated therewith in a subject in need thereof, the method comprising administering to the subject an effective amount of dofetilide, and an effective amount of mexiletine, wherein the effective amount of dofetilide is 50 mcg to 2500 mcg, and the effective amount of mexiletine is 30 mg to 600 mg.

10. The method of claim 9, wherein the mexiletine is mexiletine hydrochloride.

11. The method of claim 9, comprising administering to the subject 50 mcg to 2500 mcg dofetilide and 30 mg to 600 mg mexiletine per administration.

12. The method of claim 9, wherein the dofetilide and mexiletine are administered separately.

13. The method of claim 9, wherein the dofetilide and mexiletine are administered orally.

14. The method of claim 13, wherein the dofetilide and mexiletine are administered in one or more capsules comprising 200 mcg to 1000 mcg dofetilide and 100 mg to 500 mg mexiletine hydrochloride.

15. The method of claim 9, wherein the dofetilide and mexiletine are administered parenterally.

16. The method of claim 9, wherein the administration of the effective amount of mexiletine and the effective amount of dofetilide significantly increases atrial effective refractory period (ERP) in comparison to that achieved by the administration of the effective amount of dofetilide alone, and reduces at least one of early afterdepolarization (EAD), EAD-dependent R-on-T extrasystoles, and Torsades de Pointes (TdP) induced by the administration of the effective amount of dofetilide in the subject.

17. A method of manufacturing a pharmaceutical composition, comprising combining (a) an effective amount of dofetilide, (b) an effective amount of mexiletine, and (c) a pharmaceutically acceptable carrier to obtain the pharmaceutical composition, wherein the effective amount of dofetilide is 50 mcg to 2500 mcg, and the effective amount of mexiletine is 30 mg to 600 mg.

18. The method of claim 17, wherein the pharmaceutical composition comprises 50 mcg to 2500 mcg dofetilide and 30 mg to 600 mg mexiletine per dosage form.

19. The method of claim 17, wherein the pharmaceutical composition is a capsule, comprising 200 mcg to 1000 mcg dofetilide and 100 mg to 500 mg mexiletine hydrochloride.

* * * * *